United States Patent [19]

Riondel

[11] Patent Number: 5,919,974

[45] Date of Patent: Jul. 6, 1999

[54] PROCESS FOR THE MANUFACTURE OF AQUEOUS SOLUTIONS OF UNSATURATED QUATERNARY AMMONIUM SALTS

[75] Inventor: Alain Riondel, Forbach, France

[73] Assignee: Elf Atochem, S.A., Puteaux, France

[ * ] Notice: This patent is subject to a terminal disclaimer.

[21] Appl. No.: 08/889,370

[22] Filed: Jul. 8, 1997

[30]     Foreign Application Priority Data

Jul. 8, 1996 [FR] France ................................. 96 08477

[51] Int. Cl.$^6$ .................................................. C07C 69/52
[52] U.S. Cl. .............................................................. 560/222
[58] Field of Search ............................................ 560/222

[56]        References Cited

FOREIGN PATENT DOCUMENTS 0 329 512  8/1989  European Pat. Off. .
2 706 453  12/1994  France .

OTHER PUBLICATIONS

Patent Abstracts of Japan, vol. 7, No. 118 (C–167), JP 58037058, May 21, 1983.
Patent Abstracts of Japan, vol. 6, No. 202 (C–129), JP 57109747, Oct. 13, 1982.
Patent Abstracts of Japan, vol. 18, No. 97 (C–1167), JP 5295011, Feb. 17, 1994.
Patent Abstracts of Japan, vol. 6, No. 202 (C–129), JP 57109749, Oct. 13, 1982.
Database WPI, Section Ch, Wk. 7643, Abstract No. 76–80482X, Sep. 12, 1976.

*Primary Examiner*—Robert Gerstl

[57]        ABSTRACT

Process for the manufacture of an aqueous solution of the unsaturated quaternary ammonium salt corresponding to the following formula (I):

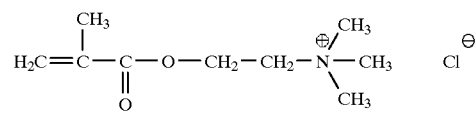

by reaction, under pressure and in the presence of water, of N,N-dimethylaminoethyl methacrylate with $CH_3$—Cl, characterized in that it is carried out in the presence of the pentasodium salt of diethylenetriaminepentaacetic acid.

20 Claims, No Drawings

PROCESS FOR THE MANUFACTURE OF AQUEOUS SOLUTIONS OF UNSATURATED QUATERNARY AMMONIUM SALTS

CROSS-REFERENCE TO RELATED APPLICATION

This application is related to a concurrently filed application entitled, "STABILIZED AQUEOUS SOLUTIONS OF UNSATURATED QUATERNARY AMMONIUM SALTS" Ser. No. 08/889,369 (Attorney Docket No. ATOCM 91), based on French Application No. 96/08476 filed Jul. 8, 1996, by Alain RIONDEL et al.

FIELD OF THE INVENTION

The present invention relates to the manufacture of an aqueous solution of the unsaturated quaternary ammonium salt corresponding to the following formula (I):

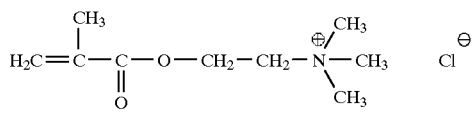

by reaction, in the presence of water, of N,N-dimethylaminoethyl methacrylate with $CH_3$—Cl as quaternizing agent.

The aqueous solutions of this salt (I) are used to prepare polymers intended to act as flocculants in water treatment.

BACKGROUND OF THE INVENTION

The above process can currently only be carried out at atmospheric pressure because the synthesis under pressure results in a thermally unstable product. However, the current process at atmospheric pressure has the disadvantage of using a larger excess of $CH_3$—Cl than if the synthesis had been carried out under pressure, the direct consequence of which is a greater gaseous discharge of $CH_3$—Cl.

Moreover, a process for the preparation of the salt (I) under pressure is known from Japanese Patent Application J 5 76-103 185. In accordance with this known process, a 50–80% (w/w) aqueous solution of a (meth)acrylate of formula:

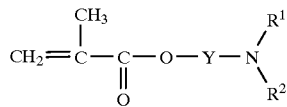

in which:
Y represents a lower alkylene or lower hydroxy-alkylene group; and
$R^1$ and $R^2$ each independently represent a lower alkyl group
is brought into contact with an alkyl or alkaryl halide in order to quaternize the above methacrylate. The only example illustrating this quaternization is carried out with addition of methyl chloride under a maximum pressure of 4.5 bar, at a temperature of 25–30° C. Besides the disadvantage, indicated above, relating to the discharge of the excess methyl chloride, this process results in significant hydrolysis of the starting compound, for example of N,N-dimethylaminoethyl methacrylate to methacrylic acid, this side reaction being promoted by the mode of introduction of the N,N-dimethylaminoethyl methacrylate and of the water, which are added already mixed and at the beginning of the reaction. This presence of methacrylic acid in the final aqueous solution obtained damages the analytical quality of the latter and can, in certain applications, have a harmful effect on its value for use in polymerization.

The aim of the present invention is to overcome the abovementioned disadvantages.

It has now been discovered, surprisingly, that the process under pressure could result in a thermally stable product, provided that it is carried out in the presence of a specific compound.

SUMMARY OF THE INVENTION

The subject of the present invention is thus first a process for the manufacture of an aqueous solution of the unsaturated quaternary ammonium salt of the formula (I) as defined above by reaction, in the presence of water, of N,N-dimethylaminoethyl methacrylate with $CH_3$—Cl as quaternizing agent, the said process being carried out under pressure, characterized in that it is carried out in the presence of the pentasodium salt of diethylenetriaminepentaacetic acid.

The pentasodium salt of diethylenetriaminepentaacetic acid is generally introduced in the proportion of 1 to 100 ppm, preferably of 5 to 30 ppm, with respect to the aqueous solution of salt (I).

The said pentasodium salt is preferentially introduced at the beginning of the reaction.

The said pentasodium salt is generally added in the form of an aqueous solution because it is mainly available in this form. Thus, the said pentasodium salt, sold under the name Versenex 80, is provided in the form of an approximately 40% by weight aqueous solution.

The reaction according to the invention is generally carried out under a pressure of 2 to 9 bar, preferably of 3 to 6 bar, and at a temperature of 35 to 65° C., in particular of 40 to 55° C.

The reaction according to the invention is, moreover, carried out with a molar ratio of $CH_3$—Cl to N,N-dimethylaminoethyl methacrylate which is generally of 1 to 1.1, preferably of 1.01 to 1.05.

In addition, at least one stabilizing agent, chosen in particular from 3,5-di-tert-butyl-4-hydroxy-toluene, hydroquinone methyl ether, hydroquinone, catechol, tert-butylcatechol and their mixtures, is advantageously used in combination with the N,N-dimethylaminoethyl methacrylate from the beginning of the reaction, in the proportion of 50 to 2000 ppm, preferably of 100 to 1000 ppm, with respect to the aqueous solution of salt (I).

A particularly preferred implementation of the process according to the invention is as follows:

(a) 5 to 15% by weight of the amount of $CH_3$—Cl necessary for the reaction are continuously introduced, at a temperature of 40–55° C., into a closed reactor which contains the N,N-dimethylaminoethyl methacrylate and the pentasodium salt of diethylenetriaminepentaacetic acid and which has been pressurized with air from 1 to 3 bar;

(b) water and the remainder of the $CH_3$—Cl are then continuously added, at a temperature of 45–55° C., until the desired concentration of salt (I) in the water is obtained, it being possible for the pressure at the end of the reaction to reach 6–9 bar; then (c) the reactor is depressurized and, after returning to atmospheric pressure, the residual $CH_3$—Cl is removed, for example by stripping with air.

The solutions have concentrations in particular of approximately 50 to 85% by weight of quaternary salt (I) in water.

The examples which will follow, given by way of information, make it possible to better understand the invention. In these examples, the percentages shown are percentages by weight and the following abbreviations have been used:

DAMEMA: dimethylaminoethyl methacrylate

Madquat MC 75: 75% aqueous methacryloyloxyethyltrimethylammonium chloride solution HQME: hydroquinone methyl ether Versenex 80: pentasodium salt of diethylenetriaminepentaacetic acid.

EXAMPLE 1

Preparation of Madquat MC 75

0.0083 g of Versenex 80 (40% aqueous solution of active materials) and 471 g of DAMEMA, stabilized with 800 ppm of HQME, are charged to a 1 l glass reactor, especially designed to take the pressure (operating pressure of $1.2 \times 10^6$ Pa (12 bar), test pressure of $6 \times 10^6$ Pa (60 bar)), equipped with a specific gas/liquid stirrer, a cooling coil, a temperature probe and a manometer, as well as a safety valve. The reactor is closed and then pressurized with 1 bar of air.

159 g of $CH_3$—Cl and 207.5 g of water are used in order to carry out the quaternization reaction of the DAMEMA, the operating conditions being: $[CH_3Cl]/[DAMEMA]=1.05$ and mean value of the ratio of $H_2O/CH_3Cl$ injection flow rate (in g/h)=0.7.

The mixture is brought to 47° C. and the introduction of liquid $CH_3$—Cl is begun at a flow rate of 40 g/h. When 10% of all the methyl chloride has been introduced (i.e. 16 g), the addition of the water is begun at a flow rate of 28 g/h, while continuing to introduce the remaining methyl chloride.

The total time for introduction of the $CH_3$—Cl is 4 hours and that of the water 7 hours. At the end of the reaction, when the addition of water is finished, the pressure reaches $6 \times 10^5$ Pa (6 bar). The reactor is then gradually depressurized while introducing an air flow, so as to have a residual gas/entering gas ratio of 1 (time:1 hour). After returning to atmospheric pressure, the residual $CH_3$—Cl is then removed while hot by stripping with air (time:30 minutes). 818 g of Madquat MC 75 are thus obtained.

The results in terms of stability on storage are combined in Table 1 below. The stability test consists in immersing, in an oil bath at 92° C., sealed test tubes 80% filled with the test product. The stability is assessed by measuring the time before polymerization.

EXAMPLE 2

Example 1 was repeated. The results are also reported in Table 1.

EXAMPLE 3

Comparative

Example 1 was repeated but without Versenex 80. The results are also reported in Table 1.

TABLE 1

| Example | Amount of Versenex 80 with respect to the final product (ppm) | Stability (hours) |
| --- | --- | --- |
| 1 | 10 | 162 |
| 2 | 10 | 168 |
| 3 (comparative) | without | 2 |

The preceding examples can be repeated with similar success by substituting the generically or specifically described reactants and/or operating conditions of this invention for those used in the preceding examples.

The entire disclosure of all applications, patents and publications, cited above, and of corresponding French application No. 96/08477, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

I claim:

1. In a process for the manufacture of an aqueous solution of the unsaturated quaternary ammonium salt corresponding to the following formula (I):

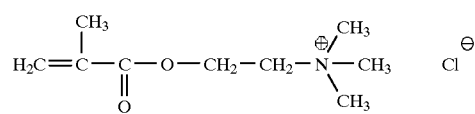

(I)

by reaction, under pressure and in the presence of water, of N,N-dimethylaminoethyl methacrylate with $CH_3$—Cl as quaternizing agent, the improvement wherein the reaction is carried out in the presence of a pentasodium salt of diethylenetriaminepentaacetic acid.

2. A process according to claim 1, characterized in the pentasodium salt of diethylenetriaminepentaacetic acid is introduced in the proportion of 5 to 30 ppm with respect to the aqueous solution of salt (I).

3. A process according to claim 1 wherein the pentasodium salt of diethylenetriaminepentaacetic acid is introduced at the beginning of the reaction.

4. A process according to claim 1 wherein the pentasodium salt of diethylenetriaminepentaacetic acid is introduced in the form of an aqueous solution.

5. A process according to claim 1 wherein the reaction is carried out under a pressure of 2 to 9 bar.

6. A process to claim 1 wherein the reaction is carried out at a temperature of 35 to 65° C.

7. A process according to claim 1 wherein the reaction is carried out with a molar ratio of $CH_3$—Cl to N,N-dimethylaminoethyl methacrylate of 1 to 1.1.

8. A process according to claim 1, wherein at least one stabilizing agent selected from the group consisting of 3,5-di-tert-butyl-4-hydroxy-toluene, hydroquinone methyl ether, hydroquinone, catechol, tert-butylcatechol and mixtures thereof, is provided in combination with the N,N-dimethylaminoethyl methacrylate from the beginning of the reaction, in a proportion of 50 to 2000 ppm, with respect to the aqueous solution of salt (I).

9. A process according to claim 1:
(a) 5 to 15% by weight of said $CH_3$—Cl necessary for the reaction is continuously introduced, at a temperature of 40–55° C., into a closed reactor which contains the N,N-dimethylaminoethyl methacrylate and the pentasodium salt of diethylenetriaminepentaacetic acid and which has been pressurized with air from 1 to 3 bar;
(b) water and remaining 85–95% by weight of $CH_3$—Cl are then continuously added, at a temperature of 45–55° C., until a desired concentration of salt (I) in the water is obtained, the pressure at the end of the reaction reaching 6–9 bar; then
(c) the reactor is depressurized and, after returning to atmospheric pressure, residual $CH_3$—Cl is removed.

10. An aqueous solution comprising the pentasodium salt of diethylenetriamine pentaacetic acid and the unsaturated quaternary ammonium salt as obtained by the process as defined in claim 1.

11. A process according to claim 5, wherein said pressure is 3 to 6 bar.

12. A process according to claim 6, wherein said temperature is 40 to 55° C.

13. A process according to claim 7, wherein said molar ratio is 1.01 to 1.05.

14. A process according to claim 8, wherein said proportion is 100 to 1000 ppm.

15. A process according to claim 9, wherein the residual $CH_3$—Cl is removed by stripping with air.

16. An aqueous solution comprising an unsaturated quaternary ammonium salt corresponding to the following formula (I):

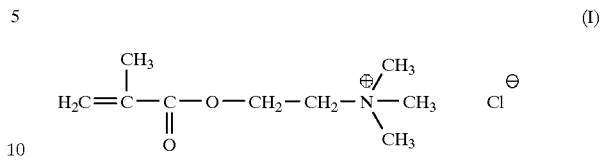

and a stabilizing amount of pentasodium salt of diethylenetriaminepentaacetic acid.

17. An aqueous solution according to claim 16, further comprising at least one stabilizing agent selected from the group consisting of 3,5-di-tert-butyl-4-hydroxy-toluene, hydroquinone methyl ether, hydroquinone, catechol, tert-butylcatechol and mixtures thereof.

18. A process according to claim 9, wherein the desired concentration of the unsaturated ammonium salt (I) is 50–85% by weight.

19. An aqueous solution according to claim 16, wherein the concentration of the unsaturated ammonium salt (I) is 50–85% by weight.

20. An aqueous solution according to claim 17, wherein the concentration of the unsaturated ammonium salt (I) is 50–85% by weight.

* * * * *